United States Patent [19]
Garner et al.

[11] Patent Number: 5,399,573
[45] Date of Patent: Mar. 21, 1995

[54] USE OF 2-SUBSTITUTED-THIAZOLIDINE-4-CARBOXYLIC ACIDS FOR TREATMENT OF CATARACT

[75] Inventors: William H. Garner, Southlake; Larry A. Wheeler, Irvine, both of Calif.

[73] Assignee: Allergan, Inc., Irvine, Calif.

[21] Appl. No.: 938,967

[22] Filed: Sep. 1, 1992

Related U.S. Application Data

[63] Continuation of Ser. No. 845,760, Mar. 3, 1992, abandoned, which is a continuation of Ser. No. 750,441, Aug. 20, 1991, abandoned, which is a continuation of Ser. No. 282,767, Dec. 9, 1988, abandoned.

[51] Int. Cl.$^6$ .............................................. A61K 31/425
[52] U.S. Cl. .................................... 514/369; 514/912
[58] Field of Search ............................... 514/369, 912

[56] References Cited

U.S. PATENT DOCUMENTS

| | | |
|---|---|---|
| 4,335,210 | 6/1982 | Meister et al. |
| 4,351,826 | 9/1992 | Clark et al. |
| 4,434,158 | 2/1984 | Meister et al. |
| 4,438,124 | 3/1984 | Meister et al. |
| 4,474,817 | 10/1984 | Clark et al. |
| 4,526,789 | 7/1985 | Clark et al. |
| 4,647,571 | 3/1987 | Meister et al. |
| 4,665,082 | 5/1987 | Meister et al. |
| 5,091,421 | 2/1992 | Clark et al. |

OTHER PUBLICATIONS

Garner, W. H., et al., "Mechanism of Delay of Galactosemic Cataract with Oxo-thiazolidine Carboxylic Acid (OTC)," Tuesday AM: Lens Poster Presentation, p. 147. (1988).

Nagasawa, H. T., et al., "2-Substituted Thiazolidine-4(-R)-carboxylic Acids as Prodrugs of L-Cysteine. Protection of Mice against Acetaminophen Heptatoxicity," J. Med. Chem,, 1984, 27, 591–596.

Holleschan, A. M., et al., "Procedures for Augmenting Glutathione in Cultured Rabbit Lenses," Lens Research, 3(1–2), 1097–118, 1986.

Roberts, T. C., et al., "Prodrugs of L-Cysteine as Protective Agents against Acetaminophen-Induced Heptatoxicity. 2-(Polyhydroxyalkyl)-and 2-(Polyacetoxylalkyl)thiazolidine-4(R)-carboxylic Acids," J. Med. Chem, 1987, 30, 1891–1896.

Chemical Abstract 114(9): 75242m, 1990. Garner et al.

*Primary Examiner*—Zohreh Fay
*Attorney, Agent, or Firm*—Robert J. Baran; Martin A. Voet; Howard R. Lambert

[57] ABSTRACT

Compounds of the formula:

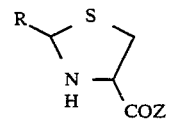

are useful for treatment of cataracts in mammals.

5 Claims, 1 Drawing Sheet

USE OF 2-SUBSTITUTED-THIAZOLIDINE-4-CARBOXYLIC ACIDS FOR TREATMENT OF CATARACT

CROSS REFERENCE TO RELATED APPLICATIONS

This application is a continuation-in-part of U.S. patent application Ser. No. 07/845,760, filed on Mar. 3, 1992, and now abandoned, which is a File Wrapper Continuation (FWC) of U.S. patent application Ser. No. 07/750,441, filed on Aug. 20, 1991, now abandoned, which is a FWC of U.S. patent application Ser. No. 07/282,767, filed Dec. 9, 1988, and now abandoned.

FIELD OF THE INVENTION The present invention relates generally to the field of diseases of the eye and particularly to certain thiazolidine compounds useful for delay of cataract.

BACKGROUND OF THE INVENTION

Several compounds in the family of 2-substituted-thiazolidine-4-carboxylates or carboxylate analogs (2-substituted-THZ) are known. One of the compounds in this family, 2-oxothiazolidine-4-carboxylic acid (OTC), has been shown to have some effect in protecting mice against acetominophen hepatotoxicity (Nagasawa, H. T., et al. *J, Med. Chem.* 1984, 27, 591–596). This compound has also been shown to have some effect in raising glutathione levels in cultured rabbit lenses in vitro (Holleschan, A. M., et al., *Lens Research*, 3(1–2), 1097–118 (1986)). However, these efforts did not demonstrate that OTC or other compounds in the THZ family had any effect on cataracts.

SUMMARY OF THE INVENTION

The present invention relates to use of 2-substituted-thiazolidine carboxylates or carboxylate analog (2-substituted THZ) for treatment of cataracts. The 2-substituted-THZ compounds of this invention have the following structure:

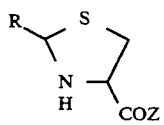

where R in the broadest embodiment is a group which in conjunction with the Z group imparts to the 2-substituted-THZ compound a hydrophobicity in terms of a partitioning coefficient (organic/aqueous) having a log P value of at least $-1$ or greater. Specifically, R may be hydrogen, hydroxy, aliphatic($C_{1-20}$), $(CH_2)_n$—Q, where n is 0–20 and Q is phenyl, thienyl, furyl, pyridyl, or $(CH_2)_n$—T where n is 0–20 and T is an aliphatic ring of 3 to 7 carbon atoms, or =O or a ketal of 2–5 carbons, or hydroxy, or 0-aliphatic ($C_{1-10}$), or $N(R_1)_2$ where $R_1$ is hydrogen or alkyl of 1 to 5 carbons, or thiazolidine, or a sugar; and Z is —OH or a pharmaceutically acceptable salt thereof, $OR_3$ where $R_3$ is an aliphatic group of 1–10 carbons, $N(R_1)_2$ when $R_1$ is hydrogen or alkyl of 1-5 carbon atoms.

Preferably R is hydrogen, =O, —OH, —SH, —$NH_2$, alkyl($Cl_{1-10}$), $(CH_2)_n$—Q wherein n is 0–10 and Q is phenyl, thienyl, furyl, pyridyl, thiazolidine, or a sugar.

More preferably R is hydrogen, methyl, ethyl, pentyl, pyridyl, =O, hydroxymethyl, tetradecyl, 4-diethylaminophenyl, thiethyl, phenyl, phenethyl, tetrahydrophenylpropyl, hydroxyphenyl, glycero, thiazolidine or one of the sugar groupsarrabino, lyxo, ribo, xylo, galacto, gluco or manno.

The 2-substituted THZ compounds of the present invention may be used to treat cataracts in mammals by administering a therapeutically effective amount of the selected compound to the mammal.

DESCRIPTION OF THE ILLUSTRATIVE EMBODIMENT

Figure 1A:
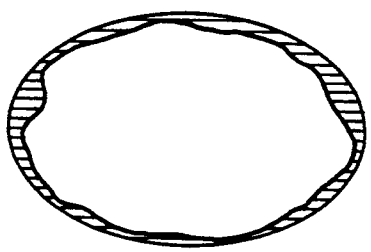
FIG. 1 shows the eyes of rats as evaluated for cataracts by a photoslit lamp and the cataracts graded as shown.

The word cataract is a general term for any pathological condition in which there is a loss of transparency of the eye. The resulting deterioration of vision in a mammal diseased with cataracts is a consequence of the loss of transparency of the lens which results from back scattering of light of detrimental modulation of light passing through the involved lens. Currently, surgical correction of a cataract is used to correct the condition by removal of the cataract diseased lens and its replacement by an intraocular lens (IOL) or alternatively by spectacles or contact lenses. However, this surgical approach has risks and therefore other efforts, such as the present invention, are directed toward development of various non-surgical treatments of cataracts.

In this regard, the compounds of the present invention, 2-substituted-thiazolidine-4-carboxylates or carboxylate analog compounds are useful for the treatment of cataracts.

The compounds of this invention contain chiral centers and accordingly, may be prepared as enantiomeric or diasteriomeric mixtures or in optically pure form. Unless otherwise specified herein, such preparations are racemates at each chiral center. However, the scope of the invention is not to be considered as limited to these forms but also to encompass the individual optical isomers of the compounds.

The substitution group, R, as shown in the 2-substituted THZ structure above, may be essentially any atom or functional group which does not render the substituted THZ compound ineffective for treatment of cataracts and does not impart any deleterious or untoward effect upon the subject to which it is administered in the context of its intended use.

Further, any pharmaceutically acceptable carboxylic acid carboxylate analog, e.g. ester, amide, or salt of the 2-substituted-THZ compound may be prepared and used for the treatment of cataracts.

Another consideration in the selection of the R group for substitution is the corneal penetration of the R-substituted THZ compound. This factor has relevance in topical application of the compound and in other contemplated 30 delivery methods. Failure of the 2-substituted THZ compound to adequately penetrate the cornea may affect the efficacy of the compound. In this regard, R-substituted compounds exhibiting some measure of hydrophobicity may exhibit better corneal penetration for topical application of the compound. The hydrophobicity of the compound may be measured in terms of its partitioning coefficient (Log P) between organic and aqueous phases. A partitioning coefficient of at least $-1$ or greater should enable the selected R-Substituted THZ compound to pass through the amphiphilic cellular membranes of lens cells via topical application.

The most preferred R-group substituents of the present invention are listed in Table I below.

TABLE I

| R group | Compound |
|---|---|
| hydrogen | |
| 2-methyl | |
| oxo- | |
| 2-hydroxymethyl-4- | |
| 2-tetradecyl-4- | |
| 2-(4-diethylaminophenyl)-4- | |
| 2-(2-thiethyl)-4- | |
| 2-(1-phenyl)-ethyl-4- | |
| 2-phenyl-4- | |
| tetrahydro-3-(1-phenylpropyl)-4- | |
| 2-(2-hydroxyphenyl)-4- | |
| 2,4- | |
| 2-nonyl-L-4- | |
| 2-ethyl-4- | |
| 2-n-pentyl-4- | |
| 2-(4-pyridyl)-4 | |
| 2-D-glycero-(1',2'-dihydroxyethyl)-4- | |
| 2-D-arabino-(1',2',3',4'-tetrahydroxybutyl)-4- | |
| 2-D-lyxo-(1',2',3'.4'-tetrahydroxybutyl)-4- | |
| 2-D-ribo-(1',2',3',4'-tetrahydroxybutyl)-4- | |
| 2-D-xylo-(1',2',3',4'-tetrahydroxybutyl)-4- | |
| 2-D-galacto-(1',2',3',4',5'-pentahydroxypentyl)-4- | |
| 2-D-gluco-(1',2',3',4',5'-pentahydroxypentyl)-4- | |
| 2-D-manno-(1',2',3',4',5'-pentahydroxypentyl)-4- |

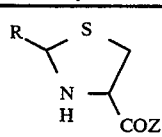

Depending on the mammal involved and delivery method utilized, e.g. topical, oral, injection, or subcutaneous, an R-group may be selected such that the efficacy of the 2-substituted-THZ compound for delay of cataract is maximized for that mammal or test subject. Accordingly, variation of the R-group, its hydrophobicity characteristics and partitioning coefficients may enable flexibility in the selection of an efficacious 2-Substituted-THZ compound within the scope of the present invention.

This list (Table I) is merely representative of the possible 2-substituted-THZ compounds contemplated by the present invention. Of course, other R-group substituents may be used in accordance with the present invention without departing from its concept.

The compounds of this invention may be delivered topically in any common ocular formulation comprising a gel, ointment, solution suspension or extended release insert. Systemic administration methods are also possible in various formulations for oral, intravenous, and subcutaneous administrations in various forms, e.g., solid, suspension or solution, as appropriate.

Pharmaceutical compositions of this invention comprise 2-substituted-THZ compounds and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a solution, gel, ointment, or the like. Standard pharmaceutical carriers for such compositions may be used. Preferably, compositions for topical administration will contain 0.05–5% of the active ingredient.

A typical cream formulation may contain the following:

| Ingredient | Parts by Weight |
|---|---|
| Water | 98–99 |
| Polyvinyl alcohol | 1–2 |
| Non-ionic surfactant | 0–10 |
| Mineral oil | 0–10 |
| Typical phamaceutical adjuvants | 0–5 |
| Active ingredient | 0.001–0.1 |
| Chlorobutenol | 0.5 |
| Sodium chloride | 0.9 |

A typical ointment formulation may contain the following:

| Ingredients | Parts by Weight |
|---|---|
| White petrolatum | 40–94 |
| Mineral Oil | 5–20 |
| Glycol solvent | 1–15 |
| Surfactant | 0–10 |
| Stabilizer | 0–10 |
| Active Ingredient | 0.05–5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
|---|---|
| Lactose, spray-dried | 40–99 |
| Magnesium stearate | 1–2 |
| Cornstarch | 10–20 |
| Active ingredient | 0.001–20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

A therapeutic (effective) concentration of 2-substituted-THZ compound for treatment of cataract is a concentration which causes delay in the onsent of cataract in a mammal having a predisposition, propensity, likelihood or possibility of forming cataract due to various etiological (cataractogenic) factors. A given therapeutic concentration may vary from individual to individual (according to the individual's needs and susceptibility to treatment), mammal to mammal, or condition to condition.

Accordingly, no single therapeutic concentration can be precisely pinpointed for treatment purposes, but will best be determined at the time and place through routine experimentation. However, it is anticipated that in treatment for the delay of cataract, an ocular or systemic formulation or dosage containing between about 0.01 mg/day/kg of a patient's body mass to about 100 mg/day/kg of patient's body mass will effectively delay the onsent of cataract. Administration may be once or several times daily depending on the concentration of the formulation being administered, the method of delivery, the patient, response to therapy, and the inherent activity of the 2-substituted-THZ containing formulation being administered.

Methods for making various 2-substituted-THZ compounds are known. Generally, these compounds may be made by condensing the corresponding aldehyde of the desired substituent with cysteine or protected cysteine, preferably L-Cysteine, in the appropriate aqueous or organic solution at a temperature of 0°–100° centigrade, preferably ambient room temperature, for a period of time from 30 minutes to overnight, but preferably from 1–2 hours.

More specifically, the method of preparation of the 2-substituted (sugar)-THZ compounds described in Table I is described by Roberts, T. C., et al., *J. Med. Chem.* 1987.30, 1891–1896. This reference also describes methods for making other 2-substituted (sugar)-THZ compounds not included in Table I but which are within the scope of the concept of the present invention.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and wherever else used, lower alkyl means having 1–6 carbon atoms. Also preferred are the phenyl or lower alkylphenyl ester.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered in the context in which it is administered.

Such a salt may be derived from any organic or inorganic base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di and trialkyl amines or ethanol amines. Salts may also be formed with caffeine, tromethamine and similar molecules. If the compound contains a nitrogen and it is sufficiently basic as to be capable of forming acid addition salts, such may be formed with any inorganic or organic acids or alkylating agent such a methyl iodide. Preferred acid addition salts are those formed with inorganic acids such as hydrochloric acid, sulfuric acid or phosphoric acid. Any of a number of simple organic acids having one, two or three carboxyl groups may be used for making acid addition salts.

If the R-group is —OH it can be converted to an ether or esters, or if a ketone, to a ketal, by known methods such as those described in *McOmie*, Plenum Publishing Press, 1973 and *Protecting Groups*, Ed. Greene, John Wiley & Sons, 1981.

EXAMPLE 1

2(RS)-Methyl-thiazolidine-4-carboxylic Acid

Acetaldehyde (0.27 g) and L-cysteine (0.75 g) were reacted in aqueous solution 10 ml at room temperature for 1.5 hours, followed by solvent evaporation evaporated in vacuo. The resulting product was recrystallized from methanol to yield the title compound. Melting Point: 161°–163° centigrade Optical Rotation $[\alpha]^{26}D$: −148°.

Other 2-substituted-thiazolidine carboxylic acids may be synthesized by substantially the same method by condensing the aldehyde corresponding to the desired R-group with 1-cysteine in a suitable aqueous or organic solution or solvent. Accordingly, a substantial range of R2-substituted-THZ compounds, such as those described in Table I above, may be synthesized.

In a like vein, the method of preparation of oxothiazolidine-4-carboxylic acid (OTC) is described by Meister, et al. in U.S. Pat. No. 4,434,158 as the method of Kaneko, et al., *Bull. Chem. Soc.* (Japan) Vol. 37, pp 242–4 (1964) as modified by the method of Shah, et al., *Cancer Research*, Vol. 39, pp. 3942–7 (1979).

A variety of 2-Substituted-THZ compounds are commercially available from various chemical manufacturers and suppliers. See for example Aldrich and Sigma. This contributes to the general availability of these compounds for study.

EXAMPLE 2

Use of 2(RS)-Substituted-Thiazolidine-4-Carboxylic Acid for Delay of Vacuolar Formation and Cataract Formation in Sprague-Dawley (albino) and Long-Evans (pigmented) Rats The 2(RS)-Substituted-Thiazolidine-4-Carboxylic Acid has been found to delay vacuolar formation and cataract formation in albino Sprague-Dawley and pigmented Long-Evans rats fed on an elevated sugar diet.

The animals (~50–100 g) were placed on a 50% galactose diet (ad lib) at 28 days of age to induce the formation of cataract. The animals were divided into several treated and untreated groups with one group remaining on normal rat chow to serve as a control group.

The compound 2-oxothiazolidine-4-carboxylic acid (OTC) was obtained from a commercial vendor and prepared in various concentrations 1, 0.1, 0.01, 0.001, and 0.0001 mg/ml in a balanced salt solution. In all treated groups, OTC treatment began on the first day of the galactose diet.

Efficacy of treatment of OTC was evaluated by several methods. In the first method, visual examination of the rats' eyes (n is 5–10 Sprague-Dawley rats) was performed daily. Ocular lenses of the examined animals were graded as follows: vacuoles in one eye (+1), vacuoles in both eyes (+2), or cataract (+3).

In a second method, slitlamp photography was used to record changes in the ocular lens of test subjects (n=5–10 rats) every couple or several days. Animals were sedated with runp injection of 100 μL Ketamine-HCl. The animals' eyes were dilated with 1 drop of Mydriacyl (tropicamid 1%) in each eye and photographs taken on a Zeiss photo slit-lamp instrument with a Nikon camera. The slip-lamp photographs of the ocular lenses of the examined animals were graded as follows: vacuoles in one eye (+1), vacuoles in both eyes (+2), or cataract (+3).

In a third evaluation method, ocular lenses of test subjects (n is 5–10 Long-Evans rats were examined every couple or several days using an Intraoptics Lens Opacity Meter 701 manufactured by Intraoptics, Inc. The animals were sedated with a rump injection of 100 μL Ketamine-HCl. The animals' eyes were dilated with 1 drop Mydriacyl (tropicamid 1%) in each eye. The animals' ocular lenses were examined using the Intraoptics Lens Opacity Meter 701 to obtain a numerical value related to the degree of lenticular density ranging in values from 0–100 with increasing light scattering in the lens. The instrument auto calibrates on start up of the instrument. The backscatter of light from the test subjects' ocular lens is measured using a modulated dark red LED 700 mm, 1.5 mm beam that runs along the axis of the lens with the results of said beam being processed by a microprocessor within the meter. Five consecutive readings were taken by the instrument for each eye with 600 total readings being taken in a given 0.5 second sampling interval. The resulting values were averaged and reported with standard deviations noted by the instrument.

Animals were divided into subgroups by method of delivery of the test compound. The corresponding test concentrations and methods are set forth in Table II below:

TABLE II

| Method of Delivery | OTC Concentration (mg/ml) |
| --- | --- |
| Systemic | |
| (1) Subcutaneous injection (20 μL; once per day) | 1, 0.1, 0.01, 0.001, 0.0001 |
| (2) Osmotic delivery with Alzet minipumps (0.5 μL/hour; continuous 24 hours/day) | 0.01, 0.001, 0.0001 |
| (3) Os (oral) gavage (100 μL of OTC in 20% Tween-20 via incubation with 20 gauge stomach syringe; once per day) | 1, 0.1, 0.01 0.001 |
| Ocular | |
| (1) Topical (drops) (OTC in 25 μL Lacrilube; twice per day) | 1, 0.1, 0.01 |

In each subgroup, OTC was found to delay vacuolar formation and cataract formation in the treated animals as compared to the untreated animals. Based on these results, efficacy may be expected from use of the other compounds named in Table I. Similarly, based on these results homologues or other R-substituted compounds not specifically named herein may be expected to be efficacious for use in delay of cataract.

EXAMPLE 3

The purpose of this experiment was to test the efficacy of the chosen compounds as well as to the comparative efficacy of each compound to OTC. This study was done on the Rat Galactosemic cataract model where Long Evans rats were fed a 30% galactose rat chow for the duration of the study.

In this experiment, compounds that may augment the natural defense mechanisms of the lens, the elevation of glutathione (GSH) levels were evaluated. The compounds chosen for this study are mainly drugs used for acetominophen toxicity. The mechanism of action of these drugs is postulated to be elevation of the cysteine pools thereby driving the rate limiting step in the natural synthesis of glutathione. The following compounds, as well as OTC and GSH, were evaluated.

γ-ECGECG is a glutathione dimer, i.e. a hexapeptide, also defined as an intracellular reductant. As such, it is believed to mimic the action of GSH in the natural defense mechanisms of the lens.
Hydroxyphenylthiazolidine (HPTHZ)
-N-Acetylcysteine (N-ACETYL CYS)
Thiazolidine Carboxylic Acid (THZ)
Methylthiazolidine Carboxilic Acid (M-THZ)
2(RS)-D-ribo(1', 2', 3', 4', tetrahydroxybutyl)thiazolidine 4(R)carboxylic acid (Rib-Cys)

L-2imidazolidone-4-carboxylic acid (IMZ) has been identified as a 5-oxyprolinase inhibitor. This compound OTC may work in its closed form. 5-Oxyprolinase is responsible for the opening of OTC intracellularly. If inhibited, OTC would stay in its naturally closed form. Efficacy of the drug would suggest that OTC may work in both closed and open forms.

Oxyproline is the natural substrate for 5-Oxyprolinase.

Twelve groups of nine rats, each, were pre-dosed with their respective regimens 24 hours prior to the administration of the galactose diet. Dosing was carried out once daily with 30 μg of compound for the duration of the experiment. The compounds were utilized in a one percent solution in one percent saponin. (Twelve groups were utilized to test the above ten compounds, as well as a galactose control, i.e. 1% saponin, only, and a control wherein no galactose was fed to the rats, i.e. 1% saponin, only.) Only the right (OD) eyes were treated. The left eyes were utilized as contralateral controls. The eyes were evaluated by photo slit lamp until all the animals showed no difference from the galactose controls. The cataracts were graded according to the scheme shown in FIG. 1. A statistical significance to the 95% confidence level was determined when compared to the galactose control.

Delay times were expressed as two values. The first value was obtained by subtracting the day where initial statistical significance between the drug treated group and the galactose control was observed, from the day where no statistical significance between the two groups was apparent. The second value, CS50, was determined by subtracting the day where the Galactose controls obtained a cataract score of 3 from the day where the drug groups obtained a cataract score of 3. This value was important to this study because at the half way point in the cataract scheme the N number was bigger and therefore allowed for better statistics. As the study progressed, the N number decreased because of nuclear study progressed, the N number decreased because of nuclear cataract formation in some animals. After formation of a bilateral nuclear cataract, the animal was excluded from the experiment. The results are reported in Table II below.

TABLE III

| DRUG | DELAY* | CS50* |
| --- | --- | --- |
| OTC | 15 | 16 |
| GSH | 6 | 2 |
| ECG | 19 | 13 |
| HPTHZ | 19 | 13 |
| N-ACETYL CYS | 9 | 8 |
| THZ | 16 | 2 |
| RIB-CYS | 10 | 12 |
| IMZ | 9 | 12 |
| OXYPROLINE | 12 | 12 |
| M-THZ | 16 | 13 |

* = Delay of nuclear cataract formation in days

All of the compounds that were chosen for this study seemed to have delayed cataract to some degree. One of the current proposed therapeutic approaches to solving the cataract problem is the elevation of glutathione pools in the lens thereby enhancing the natural defense mechanisms of the lens. However, delivering glutathione (GSH) itself topically may not be the most efficient strategy to achieve GSH elevation in the lens. This may be because of the poor systemic and corneal penetration of GSH as indicated by the relatively short delay time of GSH.

Another interesting conclusion that may be made from the data is that OTC and similar analogs may act in their comparison of the efficacy of OTC to that of N-Acetyl cysteine (a direct source of cysteine). OTC seemed to show better efficacy than that achieved by N-Acetyl cysteine. This seems to suggest that OTC may potentially act in its closed form. Since a direct source of cysteine does not delay cataract as efficiently as OTC (which is postulated to open to cysteine by 5-oxyprolinase.) OTC may in fact stay in the closed ring form. Another support for this hypothesis is the significant delay of cataractogenesis obtained from IMZ, which is stable enough to resist the cleavage of 5-Oxyprolinase. Efficacy of this drug would suggest that it is acting in the closed form.

What is claimed is:

1. A method for delaying the onset of cataract in mammals comprising administering to said mammal a composition having a therapeutically effective amount of a compound of the formula:

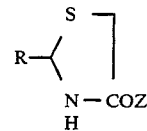

R is a hydrogen, or hydroxyphenyl, or methyl or $=O$ and Z is $-OH$ or a pharmaceutically acceptable salt thereof, $OR_3$ where $R_3$ is an aliphatic group of 1-10 carbons, $N(R_1)_2$ when $R_1$ is hydrogen or alkyl of 1-5 carbon atoms.

2. A method according to claim 1 wherein R is hydroxyphenyl.

3. A method according to claim 1 where R is a substituent group which does not detrimentally affect the efficacious activity of said compound.

4. A method according to claim 1 where R is oxo-.

5. A method according to claim 1 where R enhances the hydrophobic characteristics of said compound.

* * * * *

UNITED STATES PATENT AND TRADEMARK OFFICE
CERTIFICATE OF CORRECTION

PATENT NO. : 5,399,573
DATED : March 21, 1995
INVENTOR(S) : Garner et al

Figure 1D:
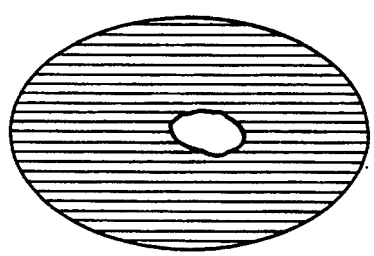
Figure 1B:
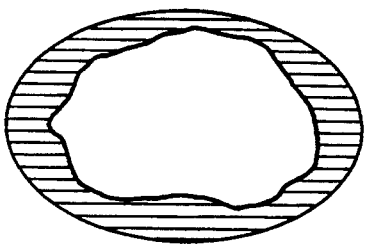
Figure 1E:
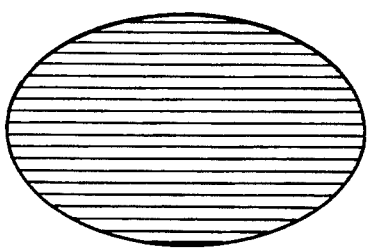
Figure 1C:
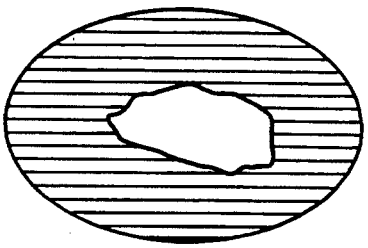
Figure 1F:
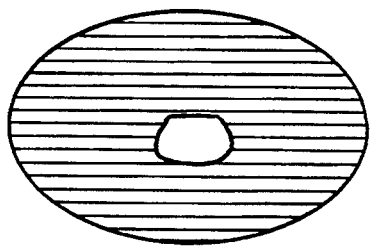

It is certified that error appears in the above-indentified patent and that said Letters Patent is hereby corrected as shown below:

Column 2, line 2; delete "groupsarrabino" and insert in place thereof --groups arrabino--
Column 2, line 58; delete "30"
Column 3, line 62; delete "ountment" and insert in place thereof --ointment--
Column 4, line 49; delete "onsent" and insert in place thereof --onset--
Column 4, line 65; delete "onsent" and insert in place thereof --onset--
Column 6, line 4; delete "R2-" and insert in place therepof --R- --
Column 6, line 49; delete "runp" and insert in place thereof --rump--
Column 8, line 14; delete "30µg" and insert in place thereof -30µ1-.
Column 8, line 25; after "FIG. 1" insert --In particular, the cataracts were graded as follows: Figure 1a. CATARACT SCORE 1 (0-10%); Figure 1b. CATARACT SCORE 2 (20-50%); Figure 1c. CATARACT SCORE 3 (50-75%); Figure 1d. CATARACT SCORE 4 (75-95% INVOLVEMENT); Figure 1e. CATARACT SCORE 5 (95-100% INVOLVEMENT); Figure 1f. NUCLEAR CATARACT (CATARACT SCORE 6).--

UNITED STATES PATENT AND TRADEMARK OFFICE
CERTIFICATE OF CORRECTION

PATENT NO. : 5,399,573
DATED : March 21, 1995
INVENTOR(S) : Garner et al

It is certified that error appears in the above-indentified patent and that said Letters Patent is hereby corrected as shown below:

Column 8, line 1; delete "2imidazolidone" and insert in place thereof
--2 imidazolidone--
Column 10, line 5 delete the formula and insert in place thereof -- 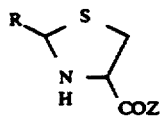 --

Signed and Sealed this

Tenth Day of October, 1995

Attest:

BRUCE LEHMAN

Attesting Officer        Commissioner of Patents and Trademarks